United States Patent
Tinnemans et al.

(10) Patent No.: US 8,553,218 B2
(45) Date of Patent: Oct. 8, 2013

(54) CALIBRATION METHOD AND APPARATUS

(75) Inventors: Patricius Aloysius Jacobus Tinnemans, Hapert (NL); Henricus Petrus Maria Pellemans, Veldhoven (NL); Gerbrand Van Der Zouw, Eindhoven (NL); Willem Marie Julia Marcel Coene, Geldrop (NL)

(73) Assignee: ASML Netherlands B.V., Veldhoven (NL)

(*) Notice: Subject to any disclaimer, the term of this patent is extended or adjusted under 35 U.S.C. 154(b) by 458 days.

(21) Appl. No.: 12/973,248

(22) Filed: Dec. 20, 2010

(65) Prior Publication Data
US 2011/0178785 A1 Jul. 21, 2011

Related U.S. Application Data

(60) Provisional application No. 61/290,310, filed on Dec. 28, 2009.

(51) Int. Cl.
*G01N 21/00* (2006.01)

(52) U.S. Cl.
USPC ..................................... 356/237.5

(58) Field of Classification Search
USPC ..................................... 356/237.5
See application file for complete search history.

(56) References Cited

U.S. PATENT DOCUMENTS

| 5,298,972 A | 3/1994 | Heffner |
| 7,277,172 B2 | 10/2007 | Kandel et al. |
| 2008/0018874 A1* | 1/2008 | Dusa et al. ........................ 355/55 |
| 2008/0239318 A1* | 10/2008 | Den Boef et al. .............. 356/369 |

FOREIGN PATENT DOCUMENTS

EP 1 628 164 A2 2/2006

* cited by examiner

*Primary Examiner* — Kara E. Geisel
*Assistant Examiner* — Dominic J Bologna
(74) *Attorney, Agent, or Firm* — Sterne, Kessler, Goldstein & Fox P.L.L.C.

(57) ABSTRACT

Calibration of an angularly resolved scatterometer is performed by measuring a target in two or more different arrangements. The different arrangements cause radiation being measured in an outgoing direction to be different combinations of radiation illuminating the target from ingoing directions. A reference mirror measurement may also be performed. The measurements and modeling of the difference between the first and second arrangements is used to estimate separately properties of the ingoing and outgoing optical systems. The modeling may account for symmetry of the respective periodic target. The modeling typically accounts for polarizing effects of the ingoing optical elements, the outgoing optical elements and the respective periodic target. The polarizing effects may be described in the modeling by Jones calculus or Mueller calculus. The modeling may include a parameterization in terms of basis functions such as Zernike polynomials.

22 Claims, 6 Drawing Sheets

CALIBRATION METHOD AND APPARATUS

CROSS REFERENCE TO RELATED APPLICATIONS

This application claims priority under 35 U.S.C. 119(e) to U.S. Provisional Patent Application No. 61/290,310, filed Dec. 28, 2009, which is incorporated by reference herein in its entirety.

BACKGROUND

1. Field of the Invention

The present invention relates to methods of calibration of optical inspection apparatus and to optical inspection apparatus such as angularly resolved scatterometers usable, for example, in the manufacture of devices by lithographic techniques.

2. Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be foamed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is necessary to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

The optical path in a scatterometer consists of three sections: the ingoing optics part having an ingoing transmission Tin; the target; and the outgoing optics part having an outgoing transmission Tout. Calibration of an angular resolved scatterometer is required to account for coordinate dependent inhomogeneities (in amplitude or phase or both) in the ingoing and outgoing optics.

It is known to calibrate a scatterometer using a known thin film reference target (for example bare Si). Thin film targets do not have diffraction orders and their reflection matrices have only diagonal elements. A zeroth order target always couples the ingoing transmission and the outgoing transmission which have the same radial coordinate in the pupil.

By using a known zeroth order target in this way, it is possible to calibrate the product of ingoing transmission Tin and outgoing transmission Tout for one combination of ingoing and outgoing rays (mirror points). If the scatterometer were only being used to measure zeroth order targets, such calibration would be sufficient. However, for scatterometry of generic targets which have diffraction orders, it is necessary to determine the product of Tin and Tout for different combinations of ingoing and outgoing coordinates. This is because there may be many customer applications for the scatterometer, with various grating pitches leading to different such combinations. Therefore the calibration should cover as many combinations of ingoing and outgoing ray paths as possible. Therefore it is important to separate Tin from Tout. This implies that we need to determine Tin and Tout separately. Currently no (in-situ) calibration approach is known that can achieve this.

The problem is to characterize these three sections individually, based upon measurements of the whole chain only. An additional complexity is also that parts of the ingoing and outgoing optics share the same optical elements (i.e., they are combined).

Known calibration methods measure the ingoing or the outgoing optics separately (or measure both separately). This requires additional hardware, and is therefore not desirable.

SUMMARY

According to a first aspect of the present invention, there is provided method of calibration of an optical inspection apparatus for inspecting a target. The optical inspection apparatus comprises at least one ingoing optical system for illuminating the target and at least one outgoing optical system for delivering radiation from the target to a detector. The method comprises the following steps. Using the ingoing optical system and the outgoing optical system in a first arrangement to obtain a first measurement of radiation in an outgoing direction, the measured radiation in the outgoing direction in the first arrangement being a combination of radiation illuminating a target from a first plurality of ingoing directions. Using the ingoing optical system and the outgoing optical system in a second arrangement to obtain a second measurement of radiation in the outgoing direction, the measured radiation in the outgoing direction in the second arrangement being a different combination of radiation illuminating a target from a second plurality of ingoing directions. Using the first and second measurements and modeling a difference between the first and second arrangements to determine separately properties of the ingoing and outgoing optical systems.

According to a second aspect of the present invention, there is provided an optical inspection apparatus for inspecting a target. The optical inspection apparatus comprises at least one ingoing optical system for illuminating the target, at least one outgoing optical system for delivering radiation from the target to a detector, and a processor configured to perform a calibration by: (a) using the ingoing optical system and the outgoing optical system in a first arrangement to obtain a first measurement of radiation in an outgoing direction, the measured radiation in the outgoing direction in the first arrangement being a combination of radiation illuminating a target from a first plurality of ingoing directions; (b) using the ingoing optical system and the outgoing optical system in a second arrangement to obtain a second measurement of radiation in the outgoing direction, the measured radiation in the outgoing direction in the second arrangement being a different combination of radiation illuminating a target from a second plurality of ingoing directions; and (c) using the first and second measurements and modeling a difference between the first and second arrangements to determine separately properties of the ingoing and outgoing optical systems.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 1:
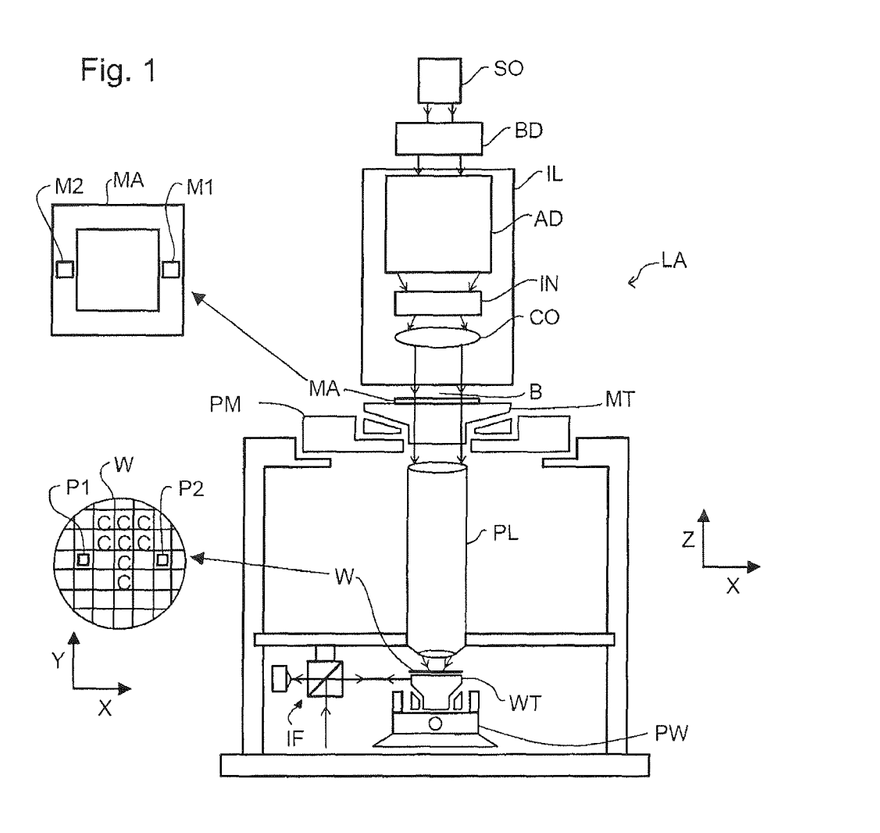
FIG. 1 depicts a lithographic apparatus.

FIG. 1 schematically depicts a lithographic apparatus. The apparatus comprises an illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist coated wafer) W and connected to a second positioner PW configured to accurately position the substrate in accordance with certain parameters, and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-) magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
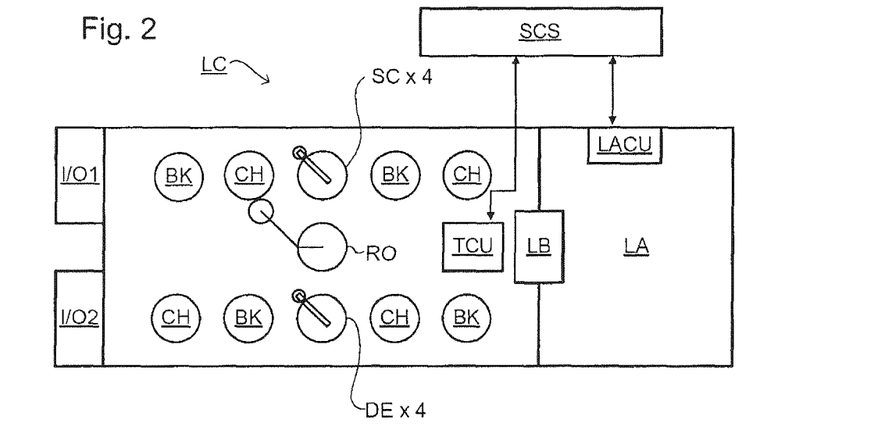
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
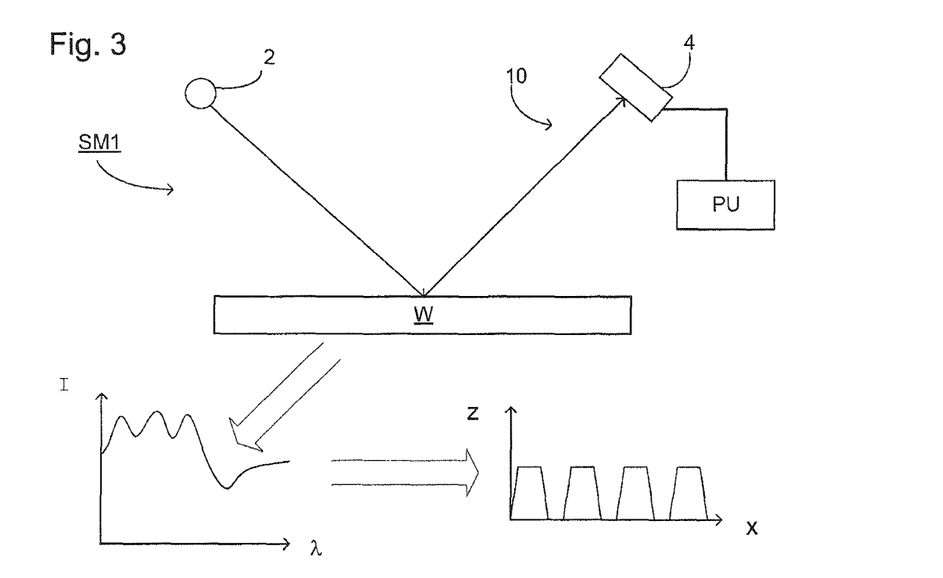
FIG. 3 depicts a first scatterometer.

FIG. 3 depicts a scatterometer. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
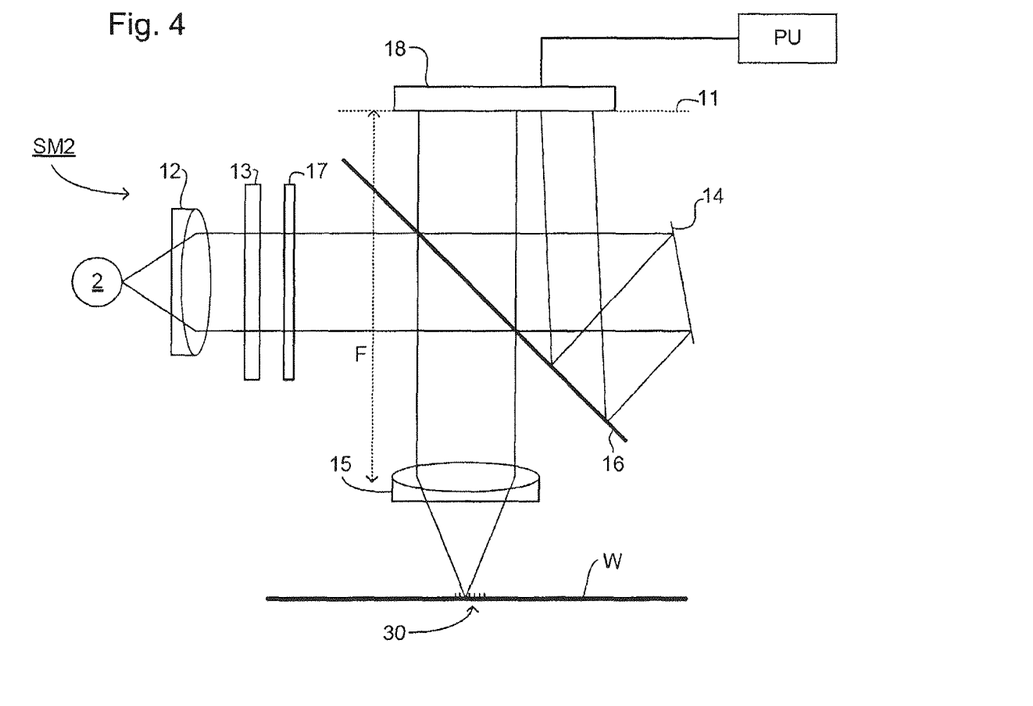
FIG. 4 depicts a second scatterometer.

A scatterometer that may be used with the present invention is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic—and transverse electric-polarized light and/or the phase difference between the transverse magnetic—and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of $\Delta\lambda$, and a spacing of at least $2\Delta\lambda$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A, which is incorporated by reference herein in its entirety.

The target 30 on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

Figure 5:
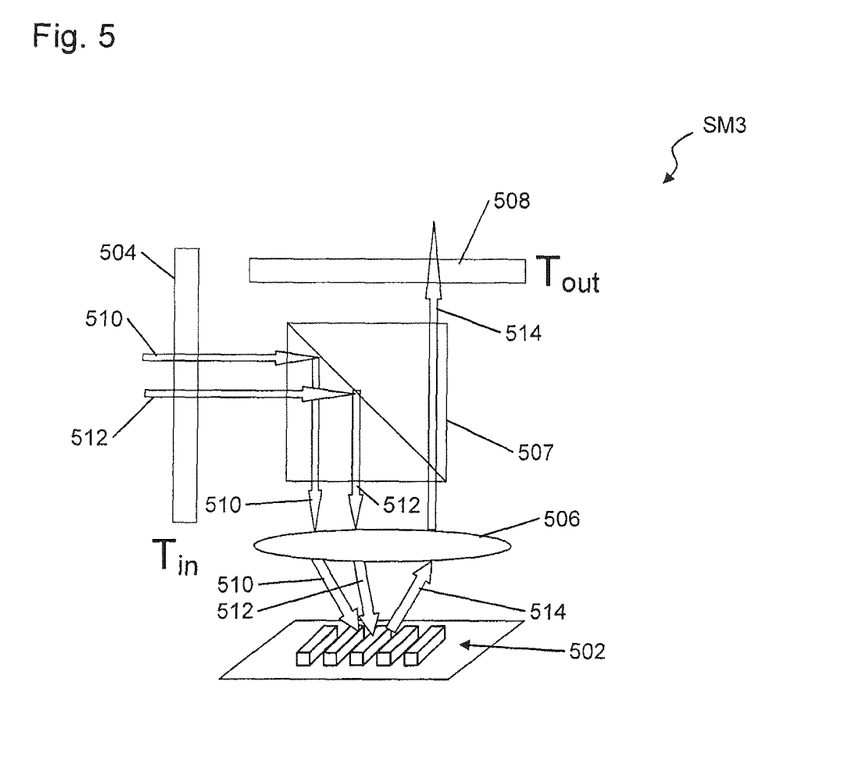
FIG. 5 illustrates a scatterometer with zeroth and first order ray paths depicted.

With reference to FIG. 5, the scatterometer SM3 measures the diffraction response of a grating 502 under multiple angles and multiple polarizations. Apart from the grating response, the recorded image also is affected by the coordinate dependent transmission (amplitude or phase or both) of the optical elements of the scatterometer itself. This transmission can be considered as a multiplicative effect of the coordinate dependent ingoing transmission $T_{in}$ of elements 504, the lens 506 (once ingoing then once outgoing) and the coordinate dependent outgoing transmission $T_{out}$ of elements 508. The lens 506 transmission is known to be polarization dependent and hence may be described by a Jones matrix. $T_{in}$ and $T_{out}$ may be assumed to be scalar, but can also be polarization dependent.

If grating 502 has pitch (period) which is larger than $\frac{1}{2}\lambda/NA$, where $\lambda$ is the measurement wavelength and NA is the numerical aperture of the system, then diffraction orders will be visible in the image. As shown in FIG. 5, multiple paths through the optics 510, 512 contribute to the same path 514 to a pixel on the camera (not shown). Thus the grating 502 effectively couples different paths through the ingoing and outgoing optical systems. In the arrangement of FIG. 5, the lens 506 contributes to both ingoing and outgoing transmission effects. Beam splitter 507 is also shown.

Inhomogeneities can occur both in the ingoing 510, 512 and outgoing 514 light paths of the scatterometer. Incorrect assignment of inhomogeneities (for example ingoing homogeneities to outgoing homogeneities) leads to incorrect scatterometer detector intensity measurements for targets 502 that generate diffraction orders (for a grating pitch larger than $\frac{1}{2}\lambda/NA$).

Figure 6:
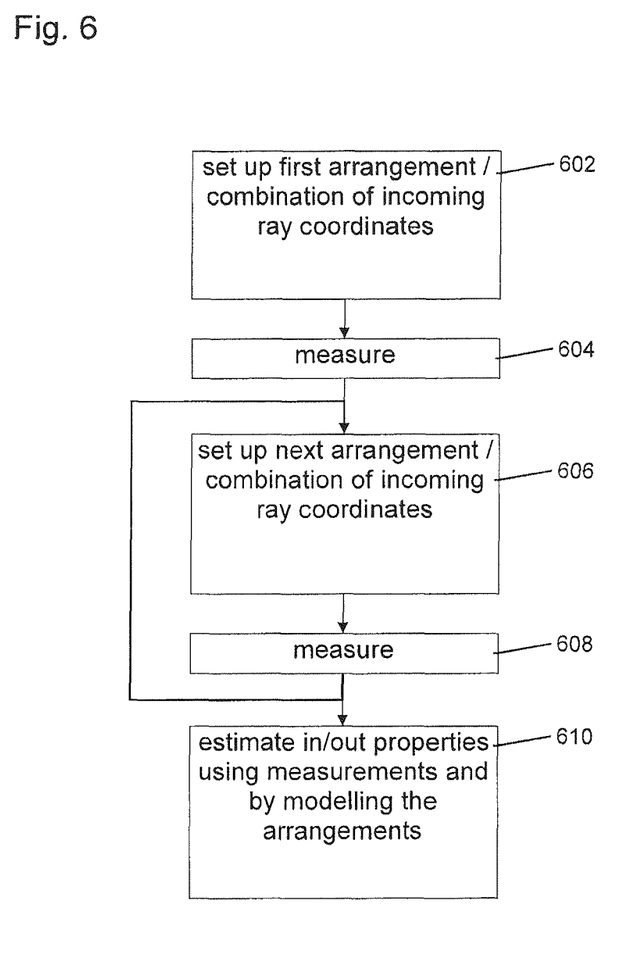
FIG. 6 is a flow chart of a calibration method according to an embodiment of the present invention.

With reference to FIG. 6, the calibration method has the steps: (a) providing 602 a first arrangement to transmit first radiation to the detector via the optical elements and via a periodic target (e.g., grating) that combines by diffraction radiation from a plurality of ingoing ray coordinates into an outgoing ray coordinate and (b) measuring 604 the first radiation using the detector. Steps (a) and (b) involve using the ingoing optical system and the outgoing optical system in the first arrangement to obtain a first measurement of radiation in an outgoing direction, the measured radiation in the outgoing direction in the first arrangement being a combination of radiation illuminating a target from a first plurality of ingoing directions.

Step (c) Providing 606 a second arrangement to transmit second radiation to the detector via the optical elements and via a periodic target that combines by diffraction radiation from a different plurality of ingoing ray coordinates into the outgoing ray coordinate. Step (d) Measuring 608 the second radiation using the detector (steps (c) and (d) can be repeated to obtain more than two arrangements). Steps (c) and (d) involve using the ingoing optical system and the outgoing optical system in the second arrangement to obtain a second measurement of radiation in the outgoing direction, the measured radiation in the outgoing direction in the second arrangement being a different combination of radiation illuminating a target from a second plurality of ingoing directions.

Step (e) estimating 610 the ingoing and outgoing optical properties separately using the measurements and modeling the effect of the arrangements on combination of radiation from ingoing ray coordinates into an outgoing ray coordinate. Step (e) involves using the first and second measurements and modeling a difference between the first and second arrangements to determine separately properties of the ingoing and outgoing optical systems.

The modeling is typically performed using a model having separate adjustable parameters describing: the ingoing optical properties as a function of ingoing ray coordinate; optical properties of the periodic target; and the outgoing optical properties corresponding to the outgoing ray coordinate. The modeling also may account for symmetry of the respective periodic target.

The modeling typically accounts for polarizing effects of the ingoing optical elements, the outgoing optical elements and the respective periodic target. The polarizing effects may be described in the modeling by Jones calculus or Mueller calculus. The modeling may include a parameterization in terms of basis functions such as Zernike polynomials. In this case, the number of different arrangements that are required is determined by the order of the basis functions that are used to expand $T_{in}$ or $T_{out}$. One needs as least as many equations (different ray path combinations) as one has unknowns (to be estimated) coefficients.

Alternatively, the modeling uses a physics-based model.

Typically, the steps of (b) measuring the first radiation, (d) measuring the second radiation, and (e) estimating are performed for a plurality of outgoing ray coordinates.

The arrangements may comprise orientations with respect to the target, such as rotation and/or tilt, of the respective radiation beam incident on the target.

Alternatively, the target in the first arrangement is different from the target in the second arrangement. Thus two or more measurements of different targets, for example having different pitch may be used, as long as they result in two or more different ray path combinations.

Providing different arrangements has two functions: it changes the combination of incoming rays contributing to the outgoing ray thus increases the number of equations; and it functions to sample a different part of the pupil plane.

When a mirror is used as a target, step (e) of estimating uses the measurement of radiation reflected by the mirror and also modeling reflection by the mirror.

In one embodiment of the present invention, the calibration approach is based upon measuring the intensity spectra of different calibration measurement gratings, which do not have to be completely known, for a number of specific rotations of these calibration measurement gratings. A sufficient set of calibration measurement gratings could for example consist of a mirror made of silicium, and a symmetrical one-dimensional grating of which only the pitch is exactly known.

By means of a mathematical algorithm in which polarizing effects of the optical elements and grating are described using Jones calculus, the measured intensities are separated in Jones matrices describing the ingoing and outgoing optics respectively.

The Jones matrices of the grating and ingoing and outgoing optical elements for each ray are expanded in terms of low spatial frequency basis functions. The Jones matrices may, for example, be represented by Zernike expansions $Z_{in}(r,\theta)$ and $Z_{out}(r,\theta)$ respectively, where r is the radius and θ is the angle.

As a basis in which to expand the Jones matrices, Zernike polynomials are used in this embodiment of the present invention for the following reasons: (a) Zernike polynomials form a well conditioned (orthogonal on the unit circle) and low spatial frequency basis; (b) Effects are to be modeled on a circular domain; (c) Zernike polynomials have proven to be well suited to describe optical effects; and (d) There are no discontinuities present in the physical effects that we want to express in terms of Zernike polynomials (that is for the ingoing and outgoing optics).

Figure 7A:
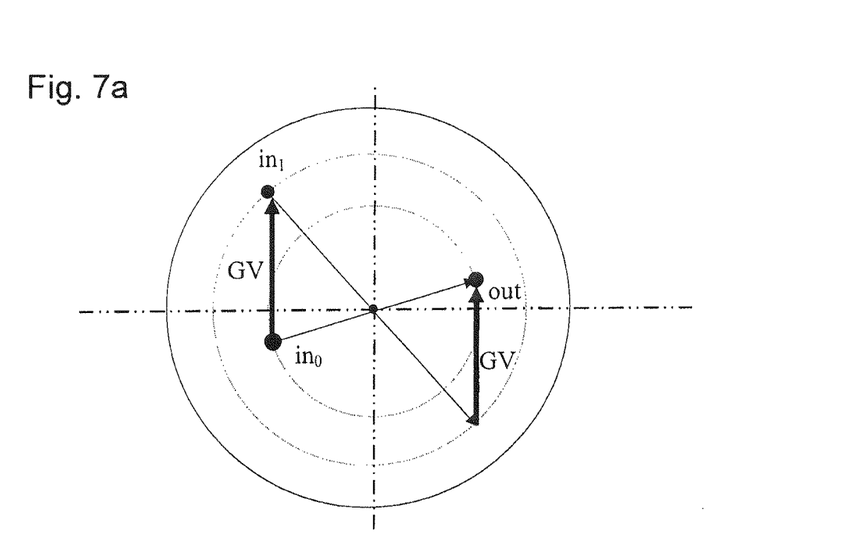
FIGS. 7a and 7b illustrate a top view through the lens of the geometry of diffraction from a grating in zeroth and first order, respectively for two stage rotations.
Figure 7B:
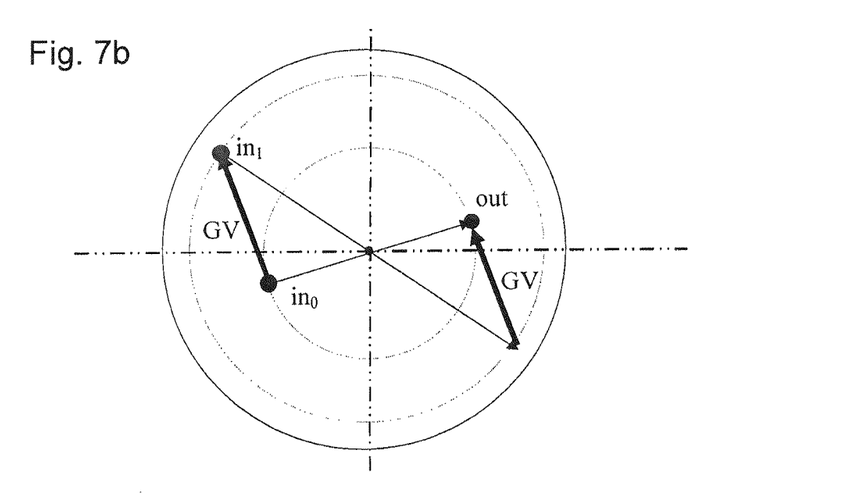

FIGS. 7a,b illustrate a method of estimating optical properties of optical elements of a scatterometer in accordance with an embodiment of the present invention. The scatterometer has ingoing optical elements having ingoing optical properties described by Jones matrices and outgoing optical elements having outgoing optical properties also described by Jones matrices.

FIG. 7a illustrates a top view through the lens of the geometry of diffraction from a grating with zeroth order and one higher diffraction order. The zeroth order ingoing point in1 and the first order ingoing point in1 are separated by the grating vector GV. The ingoing and outgoing ray "couple" a $Z_{in}$ and a $Z_{out}$. For (in$_0$, out) the coupling always occurs on the same radius and an angular separation of π. For (in$_1$, out) the coupling occurs with different angles and radii.

FIG. 7b illustrates the view like FIG. 7a, but shows the effect of wafer rotation on ray positions for one camera pixel with a grating rotation of 15° relative to the grating of FIG. 7a. This rotation has the effect that the coordinate of the first order ingoing point in1 has moved, corresponding to a changed combination of ingoing rays contributing to the outgoing ray at coordinate "out".

Figure 8:
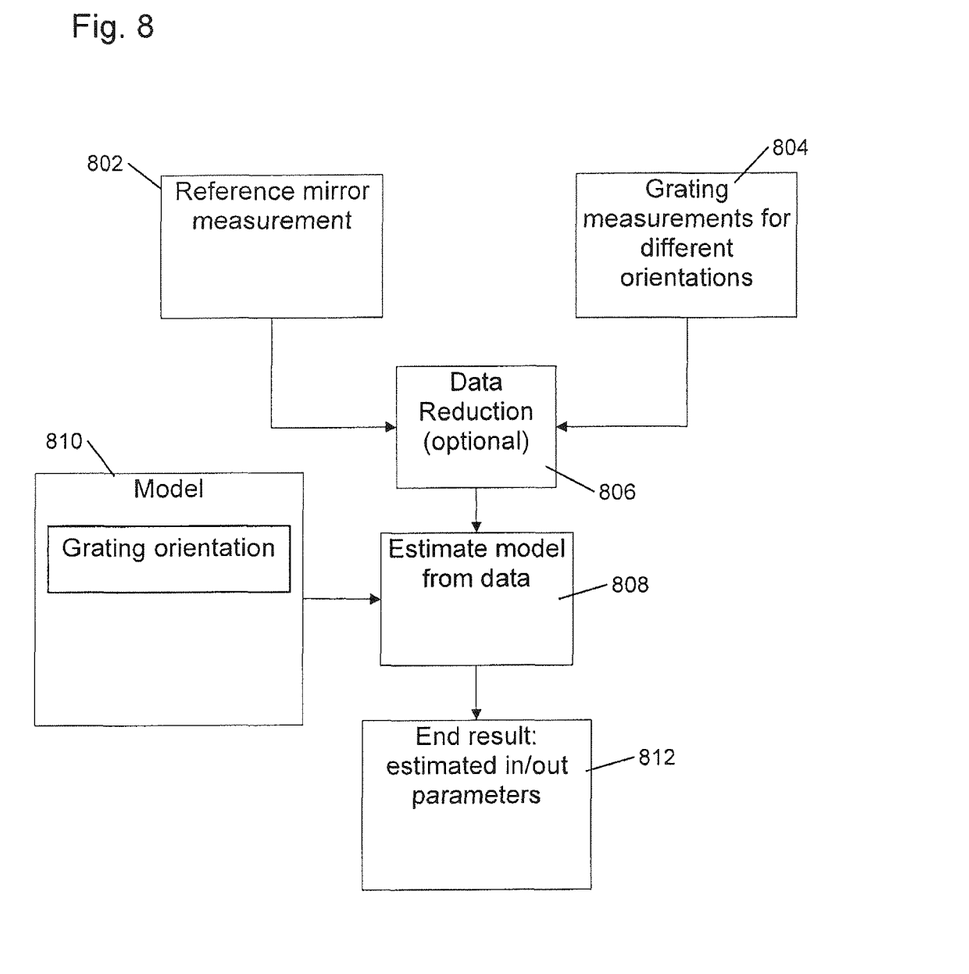
FIG. 8 is a flow chart of a calibration method according to an embodiment of the present invention.

With reference to FIG. 8, the method begins by performing a measurement 802 of a radiation beam projected via the ingoing optical elements, a reference mirror and the outgoing optical elements to obtain a zeroth order reflected pattern. The reference minor is a target without diffraction orders in the pupil. The mirror reflects radiation from an ingoing ray coordinate of the ingoing optical elements into an outgoing ray coordinate of the outgoing elements. In practice it may be a medium with planar interfaces.

Measurements are performed 804 of a radiation beam projected via the ingoing optical elements, a grating target and the outgoing optical elements to obtain a plurality of diffraction patterns, the grating measurement being repeated at a plurality of orientations of the beam with respect to the target and each of the diffraction patterns corresponding to a respective orientation. This may be performed by programmed rotation of the scatterometer wafer stage around the wafer z axis (perpendicular to the plane of the wafer). In other embodiments, other types orientations, such as tilt around the x axis or y axis (with the x and y axes in the plane of the wafer), may be programmed. Other ways of providing the plurality of orientations may be provided instead of or in addition to wafer stage movement. For example, movement of optical elements such as lenses and/or mirrors in the optical path may be used. One example would be to use a tilting and/or rotating mirror to alter the beam's path between different orientations with respect to the target.

The grating is a target with diffraction orders in the pupil. A characterized grating target may be used. It may be characterized using the same scatterometer and a method that does not require separation of the ingoing and outgoing transmission. Alternatively, the grating may be only partially known, e.g., by its symmetry, material or geometric properties.

Various measurements may be performed as follows: (a) Measure a grating that will result in some higher diffraction orders to contribute to the camera intensity as a measurement target; (b) Measure a grating that will not result in higher diffraction orders to contribute to the camera intensity as a measurement target; (c) Measure a mirror. This minor could optionally also be tilted; (d) Use more than one grating target; (e) Measure the camera intensity at multiple different camera pixels for multiple different orientations of the grating and for both horizontal and vertically polarized illumination; and (f) Measure the camera intensity also for multiple different illumination mask shapes. The ingoing transmission may be manipulated, e.g., by using apertures and/or filters.

Measurement steps 802 and 804 may be performed in any order.

An optional data reduction step 806 may be performed to reduce the number of measurement points (i.e., camera pixels).

A modeling step 808 is used to estimate the Jones matrices separately based on the measured diffraction patterns at the different stage orientations and using a model 810 to model the ingoing elements, outgoing elements, mirror, grating target and orientation of the target with respect to the beam. This step determines the model parameters 812 that optimally (in some sense) describe the measured data. The polarizing effects of the transmission and grating may be taken into account in the model 810 and described by Jones calculus, or alternatively, for example, by Mueller calculus. The end result when using Jones calculus is the estimated separate Jones matrices for the ingoing and outgoing elements.

The model 810 describes the response of the scatterometer sensor to the grating (under a plurality of orientations) and the mirror. The model also includes a mathematical description of the grating and the mirror. The model estimation may be performed for example using a least squares optimization, a maximum likelihood estimator or a least absolute deviation optimization.

The model 810 may be a parameterization in terms of mathematical basis functions, such as Zernike polynomials, as described below. Alternatively, the grating and/or mirror model may be a physics-based model, such as RCWA (rigorously coupled wave analysis).

An approach is to expand the grating response and sensor response in Zernikes, write intensity under rotations in terms of Zernikes and use a fit to solve the Zernike coefficients.

In this model for one embodiment of the present invention, we will follow a single diffracted ray while the grating is rotated. For this we will describe the intensity contribution of a diffraction order v in the wafer coordinate system. This intensity is given as function of the grating rotation angle $\theta_z$ by:

$$I_v(f'',g'',\theta_z) = T_{out}(f'',g'')T_{in}(f',g').$$

$$\text{trace}(J_o(f'',g'')J_{g,v}(f,g)J_i(f',g')\rho_{source,v}J^H_i(f',g')J^H_{g,v}(f,g) J^H_o(f'',g'')) \quad (1)$$

where (f,g) is the outgoing ray coordinate in the wafer coordinate system, (f',g') is the ingoing ray coordinate in the camera coordinate system and (f'',g'') is the ingoing ray coordinate in the camera coordinate system and (f'',g'') is the outgoing ray coordinate in the camera coordinate system. All ray coordinates are defined in terms of sine angle. Since the lens is aplanatic this corresponds to a Cartesian coordinate system in the camera.

(f',g') and (f'',g'') and (f,g) are related through the following relations:

$$\begin{bmatrix} f' \\ g' \end{bmatrix} = \theta_z \left( v \cdot \underline{\eta}_x - \begin{bmatrix} f \\ g \end{bmatrix} \right)$$

$$\begin{bmatrix} f'' \\ g'' \end{bmatrix} = \theta_z \begin{bmatrix} f \\ g \end{bmatrix}$$

where $$\theta_z = \begin{bmatrix} \cos(\theta_z) & -\sin(\theta_z) \\ \sin(\theta_z) & \cos(\theta_z) \end{bmatrix}$$

Thus, $\theta_z$ is the rotation matrix, resulting from a counter clockwise rotation of the grating around the stage rotation axis, z, by angle θz. Superscript H denotes the Hermitian transpose of the (Jones) matrix.

The grating vector, $\underline{\eta}_x$, is defined here to be equal the base vector normal to the grating lines for a one-dimensional diffraction grating, so that all reciprocal lattice vectors are integer multiples of this base vector.

In the model above we have split the ingoing/outgoing optics in a transmission part (denoted by T) and a polarization dependent part (denoted by $J_o$ and $J_i$). The grating is described by a Jones matrix $J_{g,v}$. The polarization state of the source is described by the density matrix $\rho_{source}$.

Note that the previous relations holds only for reflective diffraction (and not for transmissive diffraction) by the grating. However, although embodiments of the present invention are described in relation to reflective diffraction, the invention is also applicable to transmissive diffraction.

The grating properties that are assumed in construction of the model are:

The pitch of the grating and the illumination wavelength, λ, are known. Therefore the grating vector, $\underline{\eta}_x$, is known.

The grating rotation, $\theta_z$, is known, and this rotation, $\theta_z$, can be programmed.

The stage tilt offsets, $\theta_x$ and $\theta_y$, may be taken into account in the model and in this embodiment are known.

The grating rotation origin, i.e., $\theta_z=0$ is defined such that the grating vector, $\underline{\eta}_x$, is aligned with the camera coordinate system x-axis.

An assumption about the grating may be that because a scalar phase term in the Jones matrices of the grating does not affect the resulting camera intensity, a translation of the grating (which is assumed to be infinitely large) with respect to the origin of the coordinate system is not relevant.

Although specific reference may be made in this text to the use of inspection apparatus in the manufacture of ICs, it should be understood that the methods and inspection apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

What is claimed is:

1. A method of calibration of an optical inspection apparatus for inspecting a target, the optical inspection apparatus comprising at least one ingoing optical system for illuminating the target and at least one outgoing optical system for delivering radiation from the target to a detector, the method comprising:
   using the ingoing optical system and the outgoing optical system in a first arrangement to obtain a first measurement of radiation in an outgoing direction, the measured radiation in the outgoing direction in the first arrangement being a combination of radiation illuminating a target from a first plurality of ingoing directions;
   using the ingoing optical system and the outgoing optical system in a second arrangement to obtain a second measurement of radiation in the outgoing direction, the measured radiation in the outgoing direction in the second arrangement being a different combination of radiation illuminating a target from a second plurality of ingoing directions; and
   using the first and second measurements and modeling a difference between the first and second arrangements to determine separately properties of the ingoing and outgoing optical systems.

2. The method according to claim 1, wherein the target in the first arrangement and the target in the second arrangement comprise a grating.

3. The method according to claim 1, wherein the target in the first and second arrangements is the same target.

4. The method according to claim 1, wherein the first and second measurements are obtained in a plurality of outgoing directions.

5. The method according to claim 1, wherein the arrangements comprise orientations with respect to the outgoing direction of the target in the first and second arrangements.

6. The method according to claim 5, wherein the orientations comprise rotations.

7. The method according to claim 5, wherein the orientations comprise tilts.

8. The method according to claim 1, further comprising:
   using the ingoing optical system and the outgoing optical system in a third arrangement to obtain a third measurement of radiation in the outgoing direction, the measured radiation in the outgoing direction in the third arrangement being a reflection of radiation illuminating a mirror from an ingoing direction; and
   using the third measurement and modeling reflection by the mirror to separately determine properties of the ingoing and outgoing optical systems.

9. The method according to claim 1, wherein the modeling is performed using a model having separate adjustable parameters describing:
   properties of the ingoing optical system as a function of ingoing direction;
   diffraction properties of the target; and
   properties of the outgoing optical system corresponding to the outgoing direction.

10. The method according to claim 1, wherein the modeling accounts for symmetry of the target.

11. The method according to claim 1, wherein the modeling accounts for polarizing effects of the ingoing optical system, the outgoing optical system and the target.

12. An optical inspection apparatus comprising:
    an ingoing optical system configured to illuminate a target;
    an outgoing optical system configured to deliver radiation from the target to a detector; and
    a processor configured to perform calibration by:
      using the ingoing optical system and the outgoing optical system in a first arrangement to obtain a first measurement of radiation in an outgoing direction, the measured radiation in the outgoing direction in the first arrangement being a combination of radiation illuminating a target from a first plurality of ingoing directions;
      using the ingoing optical system and the outgoing optical system in a second arrangement to obtain a second measurement of radiation in the outgoing direction, the measured radiation in the outgoing direction in the second arrangement being a different combination of radiation illuminating a target from a second plurality of ingoing directions; and
      using the first and second measurements and modeling a difference between the first and second arrangements to determine separately properties of the ingoing and outgoing optical systems.

13. The optical inspection apparatus according to claim 12, wherein the target in the first arrangement and the target in the second arrangement comprise a grating.

14. The optical inspection apparatus according to claim 12, wherein the target in the first and second arrangements is the same target.

15. The optical inspection apparatus according to claim 12, wherein the first and second measurements are obtained in a plurality of outgoing directions.

16. The optical inspection apparatus according to claim 12, wherein the arrangements comprise orientations with respect to the outgoing direction of the target in the first and second arrangements.

17. The optical inspection apparatus according to claim 16, wherein the orientations comprise rotations.

18. The optical inspection apparatus according to claim 16, wherein the orientations comprise tilts.

19. The optical inspection apparatus according to claim 12, wherein the processor is further configured to perform calibration by:
    using the ingoing optical system and the outgoing optical system in a third arrangement to obtain a third measurement of radiation in the outgoing direction, the measured radiation in the outgoing direction in the third arrangement being a reflection of radiation illuminating a mirror from an ingoing direction; and using the third measurement and modeling reflection by the mirror to separately determine properties of the ingoing and outgoing optical systems.

20. The optical inspection apparatus according to claim 12, wherein the modeling is performed using a model having separate adjustable parameters describing:

properties of the ingoing optical system as a function of ingoing direction;

diffraction properties of the target; and properties of the outgoing optical system corresponding to the outgoing direction.

21. The optical inspection apparatus according to claim 12, wherein the modeling accounts for symmetry of the target.

22. The optical inspection apparatus according to claim 12, wherein the modeling accounts for polarizing effects of the ingoing optical system, the outgoing optical system and the target.

* * * * *